Figure 5:
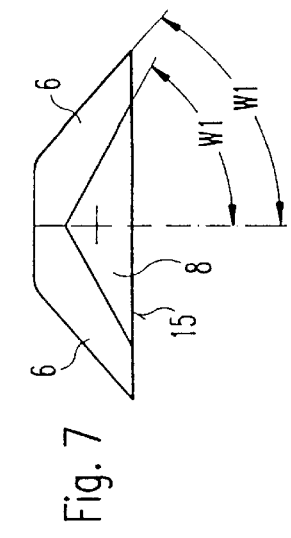

United States Patent

Hugo et al.

[19]

[11] Patent Number: 5,971,758
[45] Date of Patent: Oct. 26, 1999

[54] TOOL FOR THE PREPARATION, WITH REMOVAL OF MATERIAL, OF A LATERAL CAVITY IN A TOOTH

[75] Inventors: Burkhard Hugo, Hettstedt; Walter Mossle, Mittelbiberach, both of Germany

[73] Assignee: Kaltenbach & Voigt GmbH & Co., Biberach/Riss, Germany

[21] Appl. No.: 09/007,207

[22] Filed: Jan. 14, 1998

[30] Foreign Application Priority Data

Jan. 14, 1997 [DE] Germany .......................... 197 00 998
May 20, 1997 [DE] Germany .......................... 197 36 239

[51] Int. Cl.⁶ .................................................... A61C 1/07
[52] U.S. Cl. .......................................... 433/118; 433/165
[58] Field of Search ..................... 433/118, 119, 433/165, 166, 226

[56] References Cited

U.S. PATENT DOCUMENTS

| | | | |
|---|---|---|---|
| 2,990,616 | 7/1961 | Balamuth et al. | 433/119 |
| 3,086,288 | 4/1963 | Balamuth et al. | 433/119 X |
| 3,133,351 | 5/1964 | Von Seggern | 433/119 |
| 3,645,255 | 2/1972 | Robinson | 433/119 |
| 4,283,175 | 8/1981 | Nash | 433/119 |

FOREIGN PATENT DOCUMENTS

WO 96/14024  5/1996  WIPO.

*Primary Examiner*—Nicholas D. Lucchesi
*Attorney, Agent, or Firm*—Scully, Scott, Murphy & Presser

[57] ABSTRACT

In a tool (1) for the preparation, with the removal of material, of a lateral cavity (K) in a tooth (Z), which tool has a tool shaft (2) of which one end is connected or can be connected with a dental handpiece (4) and of which the other end is connected or can be connected with a working body (14), the longitudinal middle axis (11b) of which working body extends approximately co-axially or axis parallel to the longitudinal middle axis (11a) of the tool shaft (2), and which working body has to both sides of a longitudinal middle plane (7) extending into its longitudinal middle axis (11b), lateral working surfaces (6) which each include an acute angle with the longitudinal middle plane (7), whereby the working surfaces (6) diverge in the direction towards the tool shaft (2), the working surfaces (6) have, at least in their longitudinal region (L3) towards the tool shaft (2), or over their entire length (L), a progressive divergence (18) relative to the middle axis (11b) of the working body (14).

14 Claims, 5 Drawing Sheets

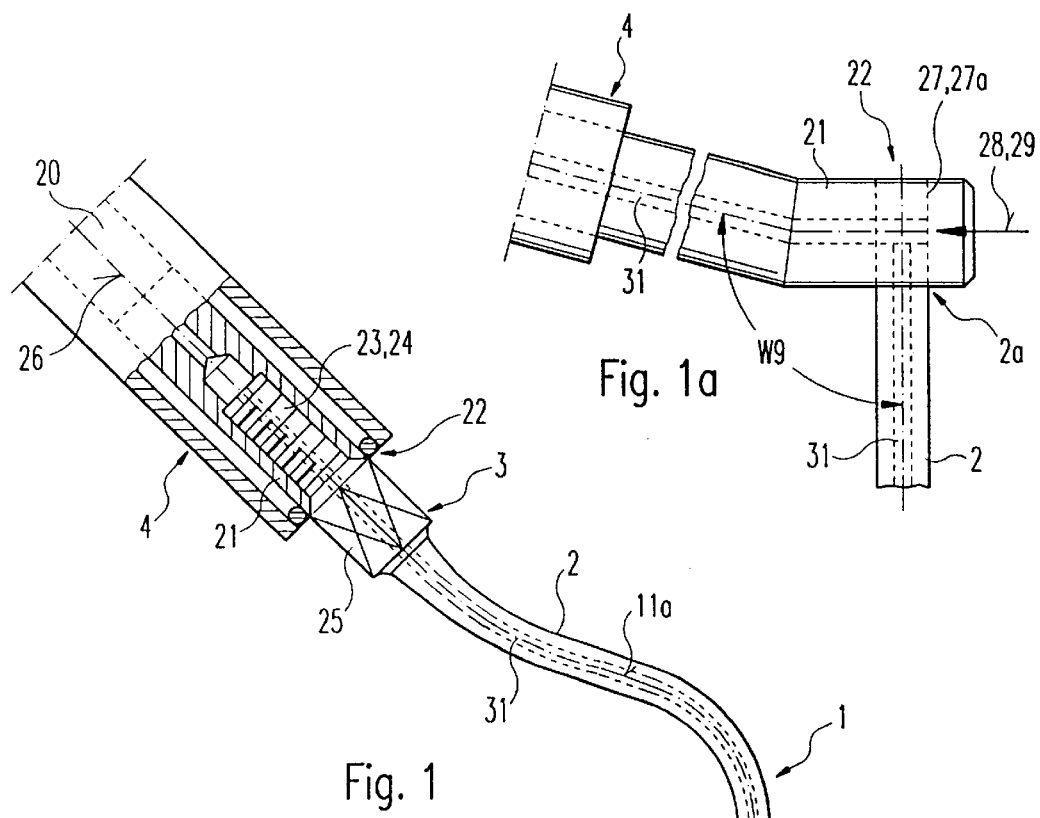
Fig. 1a
Fig. 1
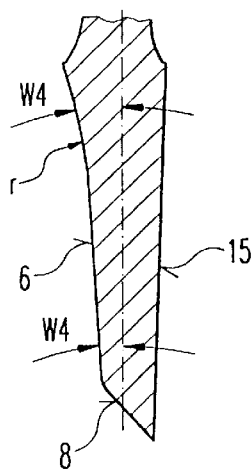
Fig. 2a
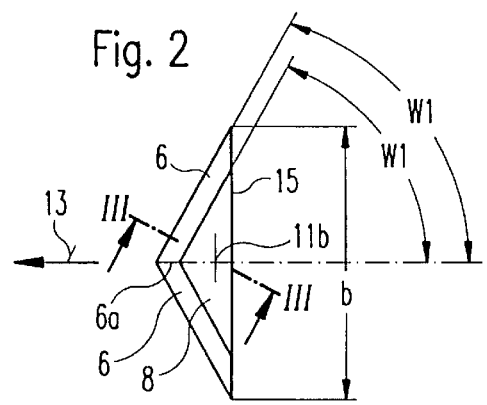
Fig. 2

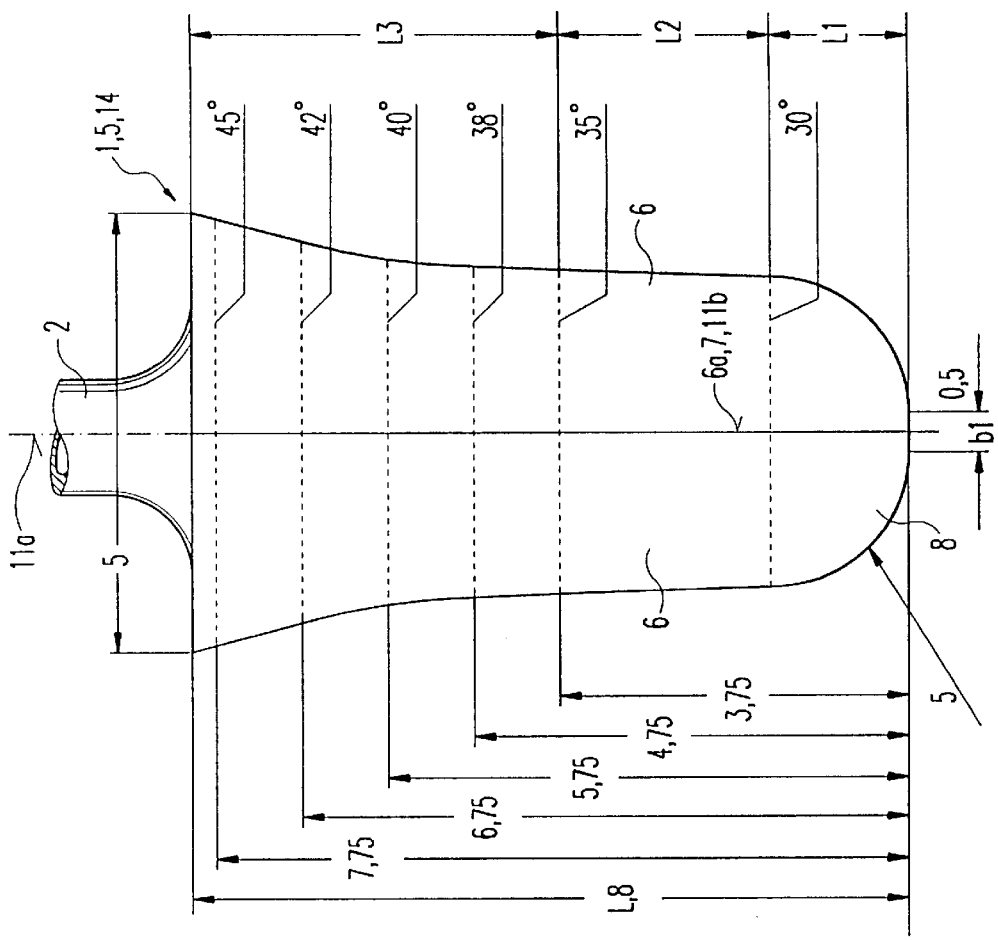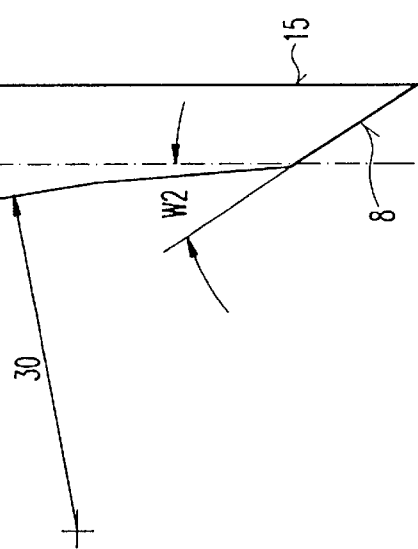

TOOL FOR THE PREPARATION, WITH REMOVAL OF MATERIAL, OF A LATERAL CAVITY IN A TOOTH

The invention relates to a tool in accordance with the preamble of claim 1 or 3.

A tool of this kind is described in WO 96/14024. There is concerned a tool the abrasive working section of which is effective laterally and at the end and is suitable, with oscillating drive in the manner of a vibration, which is transferred to the tool by means of a dental handpiece, for preparing a lateral cavity in a tooth. With this known configuration, the working section is a working head which is thickened with regard to the tool shaft of the tool and the cross-sectional form of which converges towards its free end. On the side opposite to the lateral working section, the tool has a smooth surface. By these means, the known tool is suitable to work up a cavity in the approximal region of the tooth. With this working up procedure, the working section is preferably introduced from occlusal towards cervical. Here, the cavity may already have been pre-worked by means of a rotating tool, or it can also be prepared with the working section without pre-working. Thereby, the neighbouring tooth is not affected, since the smooth surface lying opposite to the working section does not damage the neighbouring tooth. The abrasiveness of the effective working surfaces of the working section is provided by means of a lining of small grains, lying one against another, of hard material, preferably of diamonds. In functional operation, the small hard grains are effective as a multiplicity of cutters whereby the working services present are in substance effective over their entire area.

The amplitudes of the oscillation movements of the working section in functional operation can be provided by means of spatial circular or elliptical movements in the sense of vibration. In order to avoid jamming upon withdrawal of the tool from the cavity, the working section has a cross-sectional shape which converges towards its free end.

In practice it has been determined that the edge region between the outer surface of a tooth and the surfaces of a cavity running out into the outer surface is sensitive and has a tendency to break off. One believes this to result from the fact that the tooth enamel has a prism structure the prisms being bounded by imaginary rays which originate from the tooth centre. Thereby, the tooth can be thought of as a truncated egg or a truncated ball which is arranged sunk into the gum.

To avoid the breaking of the tooth enamel in the region of the edge between the cavity and the outer surface of the tooth it has already been proposed to interrupt the edge region through the provision of a chamfer and, in the preparation of the tooth, to fill this chamfer with the filling. In the case of employment of an inlay, it has already been proposed to form edge extensions on the inlay which fill the chamfer or to so shape the side surfaces and base surface of the cavity such that a desired rim angle is provided.

The above-described known tool has, to the two sides of a longitudinal middle plane running in the longitudinal direction of its working body, two edge projections on which respective chamfer working surfaces are arranged for the preparation of the chamfers at the rim edges of the cavity.

The object of the invention is to so configure a tool of the kind concerned that an advantageous shape of the walls or of the edge chamfers of the cavity can be prepared in a ready manner.

This object is achieved by the features of claim 1 or 3.

Both configurations in accordance with the invention have the common advantage that the longitudinally extending working surfaces have a shape which, taking into consideration an average tooth shape and an average width and divergence of the side walls of the cavity, make possible a favourable surface development of the surface which has been subject to abrasive working. Thereby, the tool can be used for the preparation of the edge chamfers or for the preparation of the rim regions of the surfaces of the cavity. Further, the configurations in accordance with the invention lead to a favourable development of the edges of the edge chamfers which intersect the outer surface of the tooth or of the rim region of the surfaces of the cavity, whereby favourable rim angles are provided both for a filling material of relatively little resistance to fracture such as ceramics or plastics, and a metallic filling material of greater resistance to fracture, in particular cast gold, which rim angles also lead to a small gap at the prepared tooth. The above-mentioned advantages can be achieved with a simple and ready manual guiding of the tool in the course of the working. Furthermore, the working with the tool in accordance with the invention can be carried out with little outlay in terms of time. Further, the configuration in accordance with the invention favours a preparation of improved quality.

With the configuration in accordance with the invention a tool projection intended for the preparation of the cavity itself, such as is present with the known configuration, can be omitted.

The subclaims contain features which further improve the shape of the chamfer to be prepared, contribute to stability in the edge region of the cavity and lead to a simple and economically manufacturable constructional form for the tool. Further, it is made possible that one and the same tool can be employed both in the approximal region of the tooth or in its lateral regions.

Figure 6:
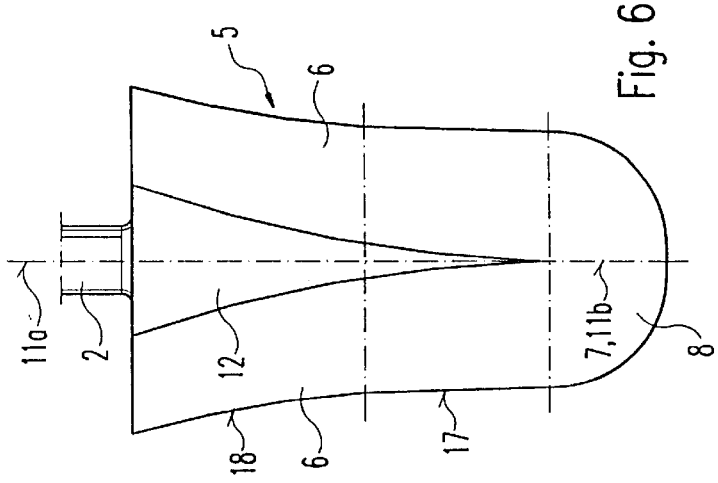
Figure 7:
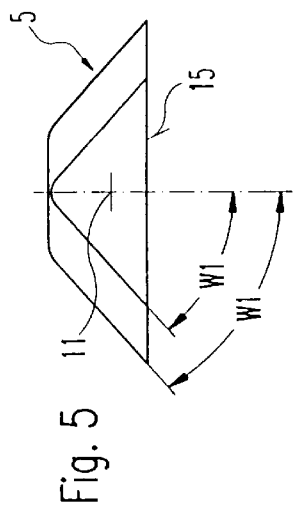
Figure 4:
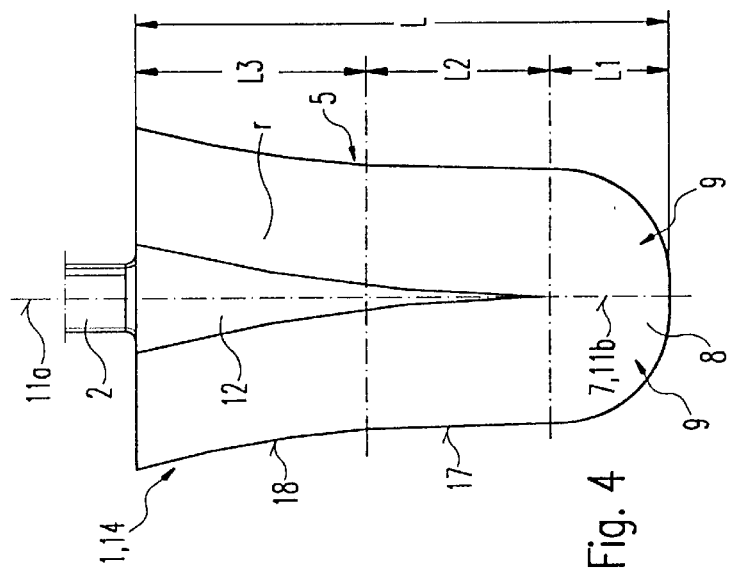
Figure 3:
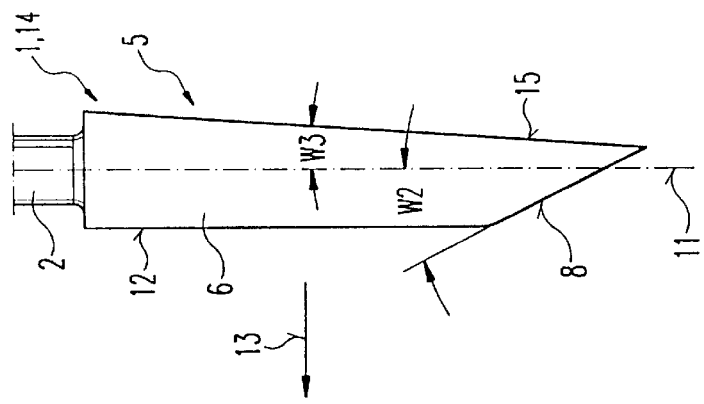
Figure 13:
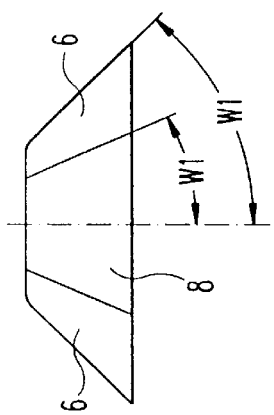
Figure 12:
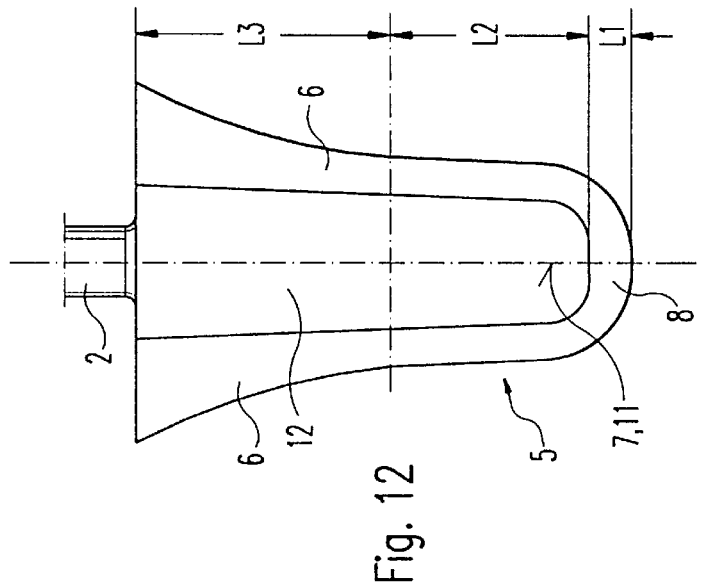
Figure 11:
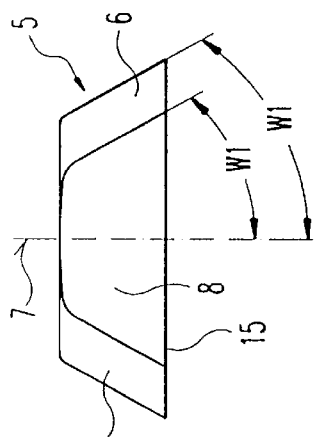
Figure 10:
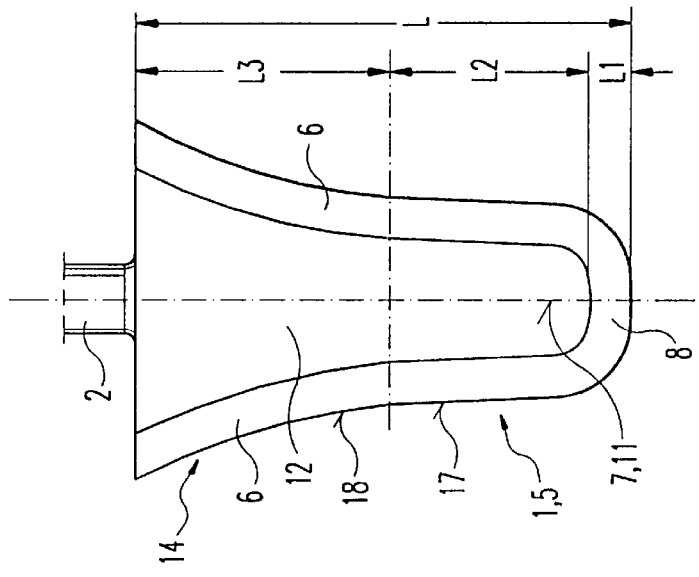
Figure 14:
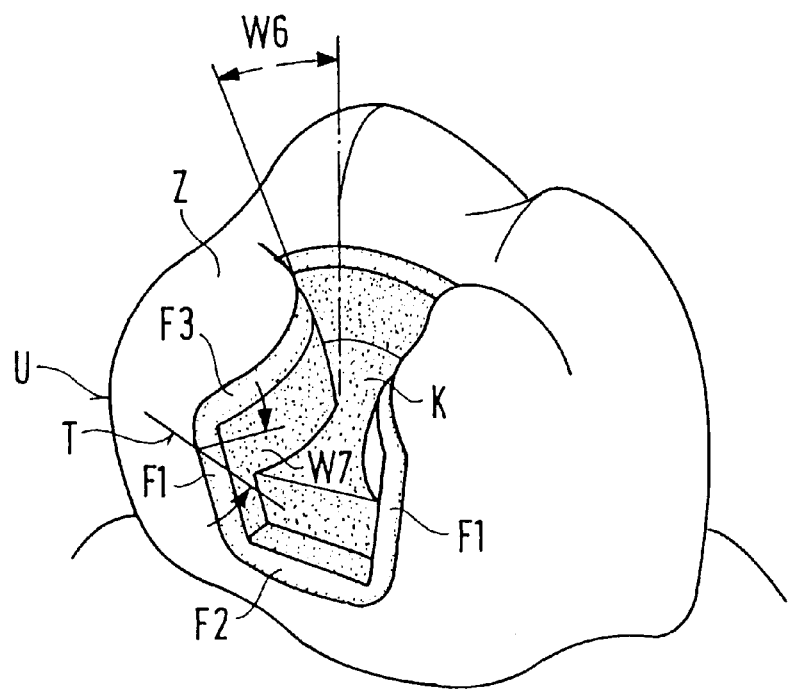
Figure 15:
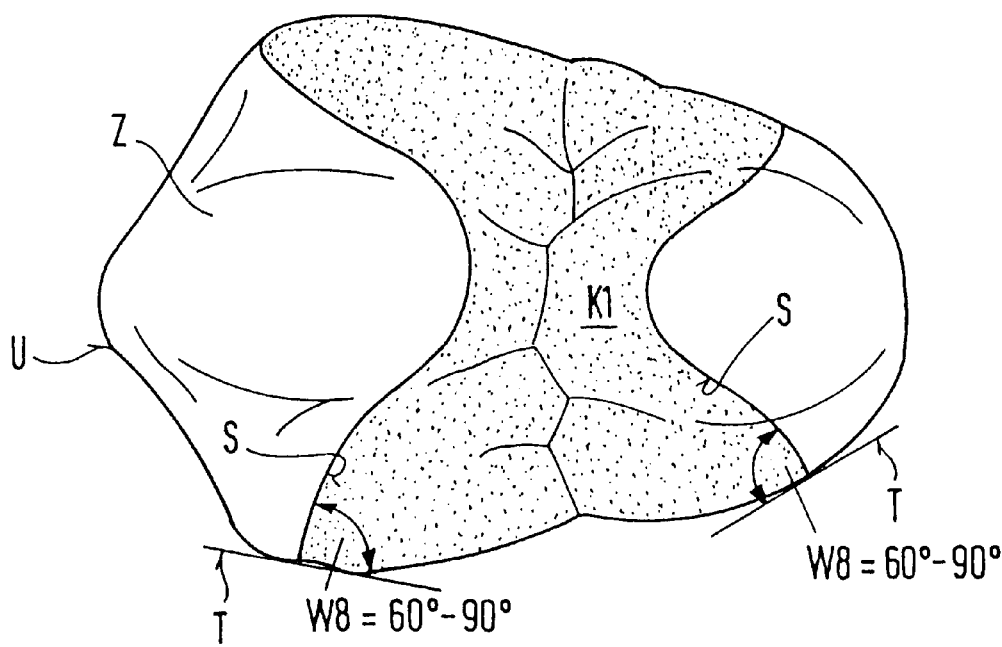

Below, the inventions and further advantages which can be achieved thereby will be described in more detail with reference to preferred exemplary embodiments and to the drawings, which show:

FIG. 1 a tool in accordance with the invention having a lateral working section, on a dental handpiece, in a side view;

FIG. 1a the tool with a dental handpiece in a modified configuration;

FIG. 2 the tool in an end view;

FIG. 2a section III—III of FIG. 2;

FIG. 3 a tool with a working section of modified configuration, illustrated in a side view and to an enlarged scale;

FIG. 4 the tool with a direction of view onto its lateral working section, in an illustration to an enlarged scale;

FIG. 5 the working section, in an end view;

FIG. 6 the tool with a direction of view onto its lateral working section, in modified configuration, illustrated to an enlarged scale;

FIG. 7 the working section according to FIG. 6, in an end view;

FIG. 8 the tool in a modified configuration, in a side view;

FIG. 9 the tool according to FIG. 8 with a direction of view onto its lateral working section, with specific dimensional indications, illustrated to an enlarged scale;

FIG. 10 the tool with a direction of view onto its lateral working section, in modified configuration, illustrated to an enlarged scale;

FIG. 11 the working section according to FIG. 10, in an end view;

FIG. 12 the tool with a direction of view onto its lateral working section, in a modified configuration;

FIG. 13 the working section according to FIG. 12, in an end view;

FIG. 14 a lower jaw tooth with a lateral or approximal cavity, in a perspective illustration;

FIG. 15 a lower jaw tooth with a lateral or approximal cavity of modified configuration, in a perspective illustration.

The tool 1 has a tool shaft 2 which has, in its end region away from the tool 1, that is, in its rear end region, at least one connection element 3 for a releasable connection with a dental handpiece 4, and which shaft is connected at its forward end releasably or non-releasably with a working body 14 which has a lateral working section 5 the working surfaces of which are abrasive, preferably occupied by a plurality of hard grains, e.g. diamond grains, as is known per se. The tool shaft 2 preferably has a round cross-sectional shape, whereby it can taper towards the working section 5 continuously or conically. The longitudinal middle axes 11a, 11b of the tool shaft 2 and of the working body 14 extend preferably coaxially or axis parallel. The working body 14 has a thickness a directed transversely of its longitudinal middle axis lib, which is approximately the same or somewhat larger than the corresponding cross-sectional dimension of the tool shaft 2, and amounts to about 2.5 mm. The breadth b of the working body 14, extending transversely of the thickness, is preferably greater than the corresponding cross-sectional dimension of the tool shaft 2, and amounts to about 4 to 5 mm. The working body 14 has thus, relative to the tool shaft 2, a is thickened working head. The length L of the working body 14, which extends in the longitudinal direction of the longitudinal middle axis 11b, amounts to about 7 to 8 mm.

The main working surfaces of the lateral working section 5 are two working surfaces 6 which are located to the two sides of a longitudinal middle plane 7 of the tool shaft 2 and of the working body 14, which plane extends into the longitudinal middle axis 11b. The working surfaces 6 extend, viewed in the transverse plane in accordance with FIG. 2, in a straight manner, whereby they each include with the longitudinal middle plane 7 an angle W1 of about 35 to 70°, in particular about 45 to 60°. The cross-sectional form of the working body 14 is trapezoidal.

The working section 5 has at its free end a third working surface 8, which extends transversely of the longitudinal middle axis 11b, which third working surface extends—in the transverse direction extending parallel to the breadth b—convexly curved, or extends in a straight manner over a part b1 of the breadth b and in the region of lateral roundings 9 transitions into the lateral working surfaces 6. The angle W2, which the working surface 8 includes with the straight longitudinal middle axis 11b, is an acute angle and it amounts to preferably about 30 to 60°, in particular about 45°. The working surfaces 6, 8 are formed to be abrasive in the sense described above. Further, a breadthwise lateral surface 12, located between the working surfaces 6 in the case of a somewhat wider working body 14 according to FIG. 4 and 5, can be correspondingly abrasive or smooth. The lateral surface 12 may extend parallel to the longitudinal middle axis 11b or be slightly inclined towards the free end. In the case of the present configuration, the lateral surface 12 is a plane surface. The working section 5 is thus arranged breadthwise on the working body 14 and formed by means of the working surfaces 6 and 8 and, if applicable, also the lateral surface 12. Its main axis or main effective direction according to arrow 13 extends in the longitudinal middle plane 7 and approximately at right angles to the longitudinal middle axis 11b.

On the side away from the main effective direction 13, the working body 14 has a smooth surface 15 which with the present configuration is a plane surface and may extend parallel relative to the longitudinal middle axis 11b (FIG. 1) or inclined towards the free end of the working body 14 (FIG. 3), whereby it may include an acute angle W3 of about 2 to 10°, in particular about 4°, with the longitudinal middle axis 11b.

As can be understood in particular from FIGS. 2a, 4 to 7, 9 and 10 to 13, the working surfaces 6 that adjoin a first longitudinal region L1 formed by means of the working surface 8 diverge in the longitudinal direction away from the free end of the working body 14, whereby in a second longitudinal region, designated L2, they have a uniform divergence 17 and, in an adjoining longitudinal region designated L3, they have a progressive divergence 18. In the region of uniform divergence 17, the working surfaces 6, extending in a straight manner, include an acute angle W4 (FIG. 2a) of in particular about 3 to 6° with the longitudinal middle axis 11b. In the region of progressive divergence 18, in which the angle 4 included between the working surfaces 6 and the longitudinal middle axis 11b is larger, the working surfaces may extend in a straight manner or concavely or curved. With the present configuration, the radius r of this curvature, which the working surfaces 6 adjoin tangentially in the region of the uniform divergence, is about 17 mm. The progressive divergence 18 may also be formed by means of a linear divergence of greater angle of inclination. When the working surfaces 6 intersect one another (no lateral surface 12 in FIG. 2), there is then provided an intersection edge 6a which is concave and diverges towards the tool shaft 2, relative to the longitudinal middle axis 11b or the smooth surface 15.

For using the tool 1 this is connected by means of the connection element 3 with a drive shaft 21 of a rod-shaped handpiece 4 in which there is arranged a schematically indicated oscillation generator or vibrator 20 which can be selectively switched on and off, which in functional operation puts the drive shaft 21 and thus also the tool 1 into vibration. The amplitudes of the oscillation or vibration can be directed substantially transversely or longitudinally of the longitudinal middle axis 26 of the handpiece, whereby they may cause circular or elliptical flat or also spatial movements of the working body 14. The frequency is preferably in the sonic or ultrasonic range.

The connection element 3 is part of a connection device 22 which in the case of the exemplary embodiment of FIG. 1 is formed by a screw connection with a threaded pin 23 arranged at the foot end of the tool shaft 2, which threaded pin can be screwed into an axial threaded bore 24 of the drive tool shaft 21. For attaching the tool there is arranged in the foot region of the tool shaft 2 an element for engagement by spanner or key, in this case a hexagon 25.

With the configuration according to FIG. 1, the free end region of the tool shaft 2 is arranged relative to the longitudinal middle axis 26 of the handpiece 4 obliquely at an acute angle W5, whereby the working body 14 is arranged laterally alongside the longitudinal middle axis 26 and thus has a lateral spacing from this axis. For this purpose, the tool shaft 2 is correspondingly bent. Preferably, the tool shaft 2 is, in its middle region, initially curved towards the side away from the working section 5 and then curved towards the working section 5 side, preferably bent, beyond the longitudinal middle axis 26. The angle W5 is preferably about 30 to 60°, in particular about 45°.

Thereby, the working section 5 is so arranged that its main direction (arrow 13) is towards or away from the handpiece 4. This arrangement is suited for the forward or rear region of a tooth to be prepared. Because of the presence of the smooth surface 15, the tool 1 is also suitable for the approximal region of a tooth, without the neighbouring tooth being substantially damaged due to the tool oscillation.

For use in the inside or outside tooth region the working section 5 is so arranged, 90° rotated on the tool shaft 2, that its direction in accordance with arrow 13 lies transversely to the longitudinal plane of the tool shaft 2 containing the angling, and this to one or to the other side (not shown). It is advantageous to associate a plurality of tools 1 with the handpiece 4, which tools may differ from one another in their shape and/or size and/or material removing capabilities, e.g. fine, coarse or fine, medium and coarse, or may differ from one another in that at least one is equipped for the forward region, at least one for the rear region, at least one for the inside and/or one for the outside region of the tooth to be prepared. In each case the working section 5 is arranged appropriately rotated.

In FIG. 14 there is illustrated a tooth Z having an occlusal cavity K, which opens out laterally or approximally of the tooth Z. For stabilisation of the tooth enamel the edges of the cavity K are interrupted by means of a chamfer. The chamfers are designated with F1 in the vertically extending edge region, the chamfer extending in the region of the base of the cavity is designated F2, and the chamfer present in the occlusal edge region is designated with F3. The cavity K can be completely worked up or only pre-worked with a rotating tool, and then worked up with a vibrationally driven abrasive tool of the kind described in the publication mentioned in the introduction. The side walls of the cavity K include an angle W6 of about 3 to 10°, in particular about 6°, with the vertical.

The present tool 1 serves for the purpose of forming the chamfers F1, F2 in the edge region between the surfaces of the cavity K and the surrounding surface U of the tooth Z. The breadth b of the working section 5 or working body 14 may be larger or smaller than the width of the cavity K. For cavities K of larger width dimensions it is advantageous to have a plurality of tools 1 of varying breadth b exchangeably available, so that they can be selectively employed. In the case of a breadth b which is greater than the width of the cavity K, the working body 14 can be introduced into the approximal region of the tooth Z from occlusal towards cervical, whereby upon introduction the chamfers F1 are first formed and at the end of the introduction movement the chamfer F2 is also formed. Thereby, the chamfers F1, F2 are given the shape predetermined by means of the shape of the working surfaces 6, 8. Insofar as subsequent finishing of the shape is desired, this can be effected by means of a renewed working of the chamfer in a correspondingly tilted position of the tool 1. When the breadth b is smaller than the width of the cavity K, then the working body 14 can be introduced from occlusal towards cervical through the free space determined by the cavity K, whereby the chamfer F2 is at least partially already worked thereby and through lateral movements of the working body 14 the chamfer F2 can be completed and the chamfers F1 worked.

Due to the progressive divergence 18 of the working surfaces 16 these have a shape which corresponds to or approximates to the edge development or the vertical edges of the cavity K. The size of the divergence preferably corresponds to an average value of the shape of the teeth, taking into account the divergence of the angle W6, or is correspondingly approximated thereto. By these means, the tool 1 is suitable for all teeth, whereby a chamfer development adapted to or approximating to the middle value is attained. There can thus be achieved a chamfer F1 of approximately the same width and of approximately the same chamfer angle W7 which is included between the chamfer F1 and a tooth tangent T, see FIG. 14.

In the preparation of a tooth with a so-called metal or cast filling, in particular cast gold filling, there are two mutually conflicting requirements. On the one hand, a chamfer is necessary for reasons of strength of the tooth enamel in the edge region. On the other hand the machining of the chamfer involves a removal of tooth material, which is not desired for reasons of tooth retention. Further, a chamfer produces an enlargement of the gap between an inlay and the walls of the cavity K because the gap is cut obliquely from the outer surface of the tooth. This is undesired because, in particular in the region in the occlusal vicinity, a cement securing the inlay is, when an enlarged gap is present, rather more open to attack and is more rapidly worn, which is undesirable.

The configurations according to FIGS. 2, 4 and 5, in which the angle W1, remaining the same over the lengths L1, L2, is about 45 to 60°, leads—with regard to the above-mentioned requirements—to an advantageous compromise. This is due to the fact that with this shape of the working surfaces 6 the actually achieved chamfer angle W7—taking into account the inclination angle W6 at the tooth Z—between the chamfer surface and the peripheral tangent T at the tooth Z, is greater in the occlusal region than in the cervical region, whereby there is provided a lesser gap of the chamfer F1 and the actual gap width at the outer wall of the tooth Z is slight. By these means, consideration is given to both the requirement for the presence of a chamfer F1, taking into account a necessary edge interruption, and also the requirement for a gap which is as small as possible. The configuration according to FIGS. 4 and 5 is thus suitable in particular for cast gold fillings.

The configuration according to FIGS. 6 and 7, in which the same or similar parts are indicated by the same reference signs, differs from the above-described exemplary embodiment in that the angle W1 from cervical to occlusal becomes uniformly or progressively smaller. By these means, the chamfer angle W7 present on the tooth Z becomes still greater, whereby the actual width of the gap at the outer surface of the tooth is further reduced, in the manner striven for.

The size of this angle change is also determined in accordance with an average value of tooth and cavity shapes and cavity widths which are normally to be treated. With the present configuration, the angle W1 is about 60° cervical and about 45° occlusal.

The configurations according to FIGS. 4 to 7 are thus suitable in particular for cast gold fillings.

FIGS. 8 and 9 show a working body 14 and a working section 5 of the configuration according to FIGS. 6 and 7, in a side view and illustrated to an enlarged scale, whereby at particular distances from the free end of the working section 5 the respective values of angles W1 which arise are indicated. Thereby, the two working surfaces 6 can intersect at a common concavely curved edge 6a or they can intersect a lateral surface 12 in accordance with FIGS. 6 and 7.

A significant difference between the exemplary embodiment according to FIGS. 10 and 11 and the exemplary embodiment according to FIGS. 4 and 5 consists in that the angle W1 is smaller and amounts to about 20 to 40°, in particular about 30°. This tool configuration is suitable for the working up of a cavity K1, FIG. 15 for a filling with a ceramics or composite material or plastics material, in particular in the case of employment of appropriate inlays or onlays, for the following reasons. In the preparation of a cavity K1 for a filling material which is less strong or can bear less loading than a metal filling, as is the case with ceramics or plastics, it is advantageous to prepare the cavity K1 without a chamfer and thereby to shape with the working surfaces 6 at least the rim regions of the side walls of the cavity K1 with an angle W8, which is bounded with a tangent T to the outer surface of the tooth Z and which increases linearly or progressively from cervical towards occlusal. With this configuration a chamfer is omitted.

The tool configurations according to FIGS. 10 to 13 are very well suited for the working up or finishing of such a cavity K1, whereby the side walls S of the cavity K1 are, at least in the outer rim region, prepared and thus shaped with the working surfaces 6. With this configuration of the working body 14 or working section 5, the working body 14 is introduced into the cavity K so that the working surfaces 6 can work the side walls S. Theoretically, the breadth b of the working body 14 can be so adapted to the desired width of the cavity K1 that the working section 5 can be introduced into the cavity, with the removal material, from the side or in the approximal region from the occlusal, with the removal of material, or the breadth b can also be made lesser so that the side walls S can be worked by means of movements of the working body to and fro. Thereby, the working surface 8, for the working of a chamfer at the base of the cavity K1, may or may not be present.

The tool configuration according to FIGS. 10 and 11, whereby the angle W1 is uniform, but the angle W4 (FIG. 2a) increases from cervical towards occlusal, provides at the side walls S of the cavity K1 a relatively small angle W8, which is desired in order to avoid a breaking of the filling or of the inlay at the rim of the cavity.

For the same reasons, the exemplary embodiment according to FIGS. 12 and 13 is also advantageous, with which embodiment the angle W1 uniformly or progressively increases from cervical towards occlusal, e.g. from about 20 to 40°, in particular about 30°, to about 35 to 55°, in particular about 45°. Due to this change of angle there is provided, taking into account the width and the angle W5 of the side walls S of the cavity K1 on the tooth Z, a approximately uniform angle W8 from cervical towards occlusal.

The free end surface of the working body 14, which in the case of the present configuration extends at an acute angle W2 and is abrasive, may run approximately at right angles with regard to the middle axis 11b and in such a case may be abrasive or, if appropriate, smooth.

With the configurations of the tool 1 and of the handpiece 4 in accordance with FIG. 1a, in which the same or similar parts are provided with the same reference signs, the tool shaft 2 extending in a straight manner is releasably held in a plug-in mounting 27 with a prismatic tool shaft end region 2a, which plug-in mounting is arranged transversely to the drive tool shaft 21 and may be formed e.g. by means of a transverse bore 27a. This drive tool shaft 21 projects forwardly beyond a housing or a grip sleeve of the handpiece 4, whereby the drive tool shaft 21 may extend axially or maybe somewhat angled, so that the tool shaft 2 includes with the longitudinal middle axis 26 of the handpiece 4 an obtuse angle W9 of e.g. about 100°. For securing the tool shaft 2 in the plug-in mounting 27 there is arranged on the drive tool shaft 21 a securing device 28 which is force-locking or form-locking, which is indicated in a simplified manner by means of an arrow 29, and which may be formed by a clamping screw which can be tensioned against the tool shaft 2.

In functional operation, the working head 14 carries out small oscillations so that all working surfaces of the working section are able to be abrasively effective and to remove the tooth material. With the present exemplary embodiment, the oscillation drive has a frequency of movement of about 4 to 8 kHz, in particular about 6 kHz, whereby in the region of the working section 5 an amplitude of e.g. spatial movements of about 0.05 mm to about 0.25 mm, in particular about 0.1 mm is provided.

The working section 5 or the tool 1 is mirror symmetrically formed around the longitudinal middle plane 7.

For the purpose of cooling the site of treatment and for the purpose of rinsing away contaminants or particles of material, it is advantageous to supply a cooling or rinsing medium, in particular water, to the site of treatment in functional operation. This can be effected by means of a supply line running, with regard to the handpiece 4 and the tool 1, externally or internally. With the present configuration, a supply line 31 extends axially through the drive tool shaft 21, through the connection device 22, axially through the tool shaft 2 up into the region of the working section 5, where it opens out in the region of at least one of the working surfaces 6, 8 or at least another surface of the working head 14. The supply line 31 has associated therewith a blocking element (not shown) for selective opening and closing. At least one outlet 32 for the supply line 31 may be arranged above the working section 5 in the tool shaft 2, from where the liquid flows automatically to the site of treatment due to gravity.

We claim:

1. A tool (1) for the preparation of a lateral cavity (K) in a tooth (Z) with the removal of material, said tool comprising a tool shaft and a working body said a tool shaft (2) having one end connectable with a dental handpiece (4) and of which the other end is connectable with said working body (14) which has a lateral triangularly cross-sectioned working section with abrasive working surfaces, the longitudinal middle axis (11b) of said working body extending approximately co-axially or axially parallel therewith or selectively following the longitudinal middle axis (11a) of the tool shaft (2) approximately co-axially or axially parallel, said working body having at both sides of a longitudinal middle plane (7) extending into the longitudinal middle axis (11b) lateral working surfaces (6) which each subtend an acute angle (W1) with the longitudinal middle plane (7), the working surfaces (6) diverging in a direction towards the tool shaft (2), and the working surfaces (6) possessing in at least a longitudinal region (L3) thereof extending towards the tool shaft (2), or selectively over their entire length (L), a progressive divergence (18) relative to the middle axis (11b) of the working body (14).

2. A tool according to claim 1, wherein the angle (W1) in at least the longitudinal region (L3) of the working surfaces (6) towards the tool shaft (2) or over the entire length (L) of the working surfaces is selectively uniform or increases or decreases in the direction towards the tool shaft (2).

3. A tool according to claim 1, wherein the progressive divergence (18) of the working surface (6) continuously increases in a direction towards the tool shaft (2).

4. A tool (1) for the preparation of a lateral cavity (K) in a tooth (z) with the removal of material, said tool comprising a tool shaft and a working body, said a tool shaft (2) having one end connectable with a dental handpiece (4) and of which the other end is connectable with said working body (14) which has a lateral triangularly cross-sectioned working section with abrasive working surfaces, the longitudinal middle axis (11b) of said working body extending approximately co-axially or axially parallel with or following along the longitudinal middle axis (11a) of the tool shaft (2), said working body having at both sides of a longitudinal middle plane (7) extending into the longitudinal middle axis (11b) lateral working surfaces (6) which each subtend an acute angle (W1) with the longitudinal middle plane (7), the working surfaces (6) diverging in a direction towards the tool shaft (2), and the angle (W1) at least in the longitudinal region (L3) of the working surfaces (6) towards the tool shaft (2) or over the entire length (L) of the working surfaces, being selectively uniform or increasing or decreasing in a direction towards the tool shaft (2).

5. A tool according to claim 4, wherein the angle (W1) selectively changes in a stepless manner or remains unchanged.

6. A tool according to claim 4, wherein the angle (W1) is within the range of about 30 to 60°.

7. A tool according to claim 4, wherein in a longitudinal region (L3) proximate the shaft the angle (W1) is about 45° and in a longitudinal region (L2) distant from the shaft about 60°.

8. A tool according to claim 4, wherein in a longitudinal region (L3) proximate the shaft the angle (W1) is about 45° and in a longitudinal region (L2) distant from the shaft about 30°.

9. A tool according to claim 1 or 4, wherein in a longitudinal region (L1) of the working section (5) distant from the tool shaft there is provided a chamfer working surface (8) which develops transversely and transitions smoothly into the longitudinally developing working surfaces (6).

10. A tool according to claim 9, wherein the transversely extending working surface (8) subtends with the longitudinal middle axis (11) of the working section (5) an acute angle of about 30° which opens towards the tool shaft (2).

11. A tool according to claim 9, wherein the transversely working surface (8) extends in a middle transverse region (b1) straight in a transverse direction.

12. A tool according to claim 1 or 4, wherein the working surfaces (6) in longitudinal extent selectively intersect each other or intersect a lateral surface (12) of the working section (5).

13. A tool according to claim 1 or 4, wherein said tool has a smooth surface (15) on a side opposite to the lateral working surfaces (6).

14. A tool according to claim 13, wherein the surface (15) extends axially parallel with the longitudinal middle axis (11) or is inclined towards the free end (angle W3) and is planar.

* * * * *